(12) United States Patent
Shuros et al.

(10) Patent No.: US 9,278,217 B2
(45) Date of Patent: *Mar. 8, 2016

(54) SYMPATHETIC STIMULATION FOR IMPROVED MYOCARDIAL RELAXATION

(71) Applicant: Cardiac Pacemakers, Inc., St. Paul, MN (US)

(72) Inventors: Allan C. Shuros, St. Paul, MN (US); Shantha Arcot-Krishnamurthy, Vadnais Heights, MN (US); Guy Alvarez, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 170 days.

This patent is subject to a terminal disclaimer.

(21) Appl. No.: 13/952,933

(22) Filed: Jul. 29, 2013

(65) Prior Publication Data

US 2013/0310889 A1 Nov. 21, 2013

Related U.S. Application Data

(63) Continuation of application No. 13/019,818, filed on Feb. 2, 2011, now Pat. No. 8,498,704.

(60) Provisional application No. 61/300,904, filed on Feb. 3, 2010.

(51) Int. Cl.
*A61N 1/365* (2006.01)
*A61N 1/362* (2006.01)

(52) U.S. Cl.
CPC ............ *A61N 1/36564* (2013.01); *A61N 1/365* (2013.01); *A61N 1/3621* (2013.01)

(58) Field of Classification Search
CPC . A61N 1/3621; A61N 1/36564; A61N 1/365; A61N 1/36571
See application file for complete search history.

(56) References Cited

U.S. PATENT DOCUMENTS 5,196,204 A * 3/1993 Jackson et al. ................ 424/538
5,800,464 A 9/1998 Kieval
6,690,971 B2 2/2004 Schauerte et al.
(Continued)

FOREIGN PATENT DOCUMENTS

FR 2753722 A1 3/1998
WO WO-9813518 A1 4/1998
(Continued)

OTHER PUBLICATIONS

"U.S. Appl. No. 13/019,818, Non Final Office Action mailed Oct. 24, 2012", 17 pgs.
(Continued)

*Primary Examiner* — Catherine Voorhees
(74) *Attorney, Agent, or Firm* — Schwegman Lundberg & Woessner, P.A.

(57) ABSTRACT

Described are methods and devices for improving diastolic function with electrostimulation in heart failure patients who exhibit relatively normal systolic function. Such patients are characterized by impaired myocardial relaxation during diastole that prevents adequate filling of the ventricles during diastole to thereby reduce cardiac output. An implantable device is described for effecting strategic and periodic stimulation of the sympathetic nervous system to elicit myocardial adrenergic activation for improved myocardial relaxation.

18 Claims, 4 Drawing Sheets

(56) References Cited

U.S. PATENT DOCUMENTS

| | | | |
|---|---|---|---|
| 6,937,896 B1 | | 8/2005 | Kroll |
| 7,096,064 B2 | | 8/2006 | Deno et al. |
| 7,218,964 B2 | | 5/2007 | Hill et al. |
| 7,526,338 B1 | | 4/2009 | Gill |
| 8,498,704 B2 | * | 7/2013 | Shuros et al. ............ 607/19 |
| 2003/0100845 A1 | | 5/2003 | Eide |
| 2006/0167516 A1 | * | 7/2006 | Kjellstrom et al. ......... 607/23 |
| 2006/0287604 A1 | | 12/2006 | Hickey |
| 2007/0191901 A1 | * | 8/2007 | Schecter ................ 607/17 |
| 2007/0203522 A1 | | 8/2007 | Hettrick et al. |
| 2007/0203527 A1 | | 8/2007 | Ben-David et al. |
| 2007/0288070 A1 | | 12/2007 | Libbus et al. |
| 2008/0021504 A1 | * | 1/2008 | McCabe et al. ............ 607/9 |
| 2008/0065158 A1 | | 3/2008 | Ben-Ezra et al. |
| 2008/0200960 A1 | * | 8/2008 | Libbus ................ 607/14 |
| 2008/0294216 A1 | * | 11/2008 | Jarverud et al. .......... 607/25 |
| 2009/0234406 A1 | | 9/2009 | Shuros et al. |
| 2011/0190840 A1 | | 8/2011 | Shuros et al. |
| 2012/0046299 A1 | | 2/2012 | Belardinelli et al. |

FOREIGN PATENT DOCUMENTS

| | | |
|---|---|---|
| WO | WO-2007064261 A1 | 6/2007 |
| WO | WO-2011097293 A1 | 8/2011 |

OTHER PUBLICATIONS

"U.S. Appl. No. 13/019,818, Notice of Allowance mailed Apr. 4, 2013", 10 pgs.

"U.S. Appl. No. 13/019,818, Response filed Jan. 24, 2013 to Non Final Office Action mailed Oct. 24, 2012", 11 pgs.

"U.S. Appl. No. 13/019,818, Restriction Requirement mailed Aug. 29, 2012", 6 pgs.

"International Application Serial No. PCT/US2011/023468, Search Report mailed Apr. 21, 2011", 4 pgs.

"International Application Serial No. PCT/US2011/023468, International Preliminary Report on Patentability mailed Aug. 16, 2012", International Preliminary Report on Patentability, 8 pgs.

"International Application Serial No. PCT/US2011/023468, Written Opinion mailed Apr. 21, 2011", 8 pgs.

* cited by examiner

SYMPATHETIC STIMULATION FOR IMPROVED MYOCARDIAL RELAXATION

CLAIM OF PRIORITY

This application is a continuation of U.S. application Ser. No. 13/019,818, filed Feb. 2, 2011, now issued as U.S. Pat. No. 8,498,704, which claims the benefit of priority under 35 U.S.C. §119(e) of U.S. Provisional Patent Application Ser. No. 61/300,904, filed on Feb. 3, 2010, each of which is herein incorporated by reference.

BACKGROUND

Heart failure (HF) refers to a clinical syndrome in which an abnormality of cardiac function causes a below normal cardiac output that can fall below a level adequate to meet the metabolic demand of peripheral tissues. It can be due to a variety of etiologies with ischemic heart disease being the most common. Heart failure is usually treated with a drug regimen designed to augment cardiac function and/or relieve congestive symptoms. It has also been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT).

The treatments for HF discussed above are most appropriately used to treat patients with systolic dysfunction. In such patients, the fraction of the blood accumulated during diastolic filling of one or both ventricles that is pumped out during systole, referred to as the ejection fraction (EF), is below normal. Some HF patients, however, are shown to maintain a normal left ventricular EF. Of the more than 5 million Americans who have heart failure (HF), 30% to 50% have HF with preserved ejection fraction (HF-PEF). HF-PEF is associated with high morbidity and mortality, and HF-PEF commonly occurs in elderly patients with comorbidities of hypertension, left ventricular hypertrophy, diabetes, myocardial ischemia, and obesity. Although the mechanisms of HF with a normal EF are incompletely understood, diastolic dysfunction is a central component, leading to it also being referred to as diastolic heart failure (DHF). Current treatment modalities have improved the prognosis among individuals with HF and a depressed EF but have not been as successful in patients with HF-PEF.

DETAILED DESCRIPTION

Described herein are methods and devices for improving diastolic function in HF-PEF patients with electrostimulation. HF-PEF is characterized by a stiff LV myocardium where myocardial relaxation (lusitropy) is impaired during diastole. The decreased lusitropy prevents adequate filling of the ventricles during diastole to thereby reduce cardiac output. An implantable device is described for effecting strategic and periodic stimulation of the sympathetic nervous system to elicit myocardial adrenergic activation for improved myocardial relaxation.

The molecular basis for the treatment just described is as follows. An increase in calcium uptake by cardiomyocytes leads to increased myocardial contractility (positive inotropic effect), while myocardial relaxation, or lusitropy, decreases. Relaxation of the heart is negatively impacted by the following factors: too much intracellular calcium, a decreased rate of calcium efflux via cellular pumps so that calcium is not removed from the cell quickly enough, an impaired sarcoendoplasmic reticulum calcium ATPase (SERCA) that, in the myocyte, pumps calcium from the cytoplasm of the cell into the endoplasmic reticulum, and an increased TN-C binding affinity, where TN-C (troponin-C) is a protein that affects the myosin-actin fibers of the heart such that when calcium binds, it triggers contraction of the heart. Near the end of the cycle of excitation-contraction coupling in the myocyte, the sarcoplasmic reticulum actively sequesters Ca++ so that the concentration of Ca++ in the vicinity of troponin-C is reduced allowing the Ca++ to leave its binding sites on the troponin-C and thereby permit disengagement of actin from myosin. This is a necessary step to achieve rapid and complete relaxation of the myocyte. If this mechanism is impaired (e.g., by reduced rate of Ca++ uptake by the sarcoplasmic reticulum), then the rate and perhaps the extent of relaxation are decreased. This will reduce the rate of ventricular filling, particularly during the phase of rapid filling.

Myocardial beta-adrenergic receptor stimulation (i.e., via sympathetic stimulation) causes activation of protein kinase A (PKA) which then phosphorylates to cardiac proteins, troponin I (TNI) and phospolamban. Phosphorylation of TNI by PKA desensitizes the myofilament to Ca2+, increases the off rate of Ca2+ from troponin, and speeds cross-bridge cycling. Phophorylation of phospholamban removes the inhibitory effect of phospholamban on SERCA leading to activation and expression of SERCA. Both mechanisms contribute to faster sequestration of Ca++ into the sarcoplasmic reticulum thereby enhancing relaxation and reloading of the sarcoplasmic reticulum for subsequent beats. Electrostimulation delivered at selected myocardial or neural sites so as to cause stimulation of myocardial beta-adrenergic receptors may thus be employed to improve lusitropy and cardiac function in HF-PEF patients. In an exemplary embodiment, one or more stimulation electrodes are implanted at such selected sites and connected to an implantable cardiac device incorporating pulse generation circuitry such as described herein via leads. The stimulation electrodes may be disposed in or on the heart or near neural tissue of the sympathetic nervous system that innervate the heart. Examples of stimulation sites for producing sympathetic stimulation include spinal cord tissue at the cervicothoracic spinal levels (e.g., C1-C8; T1-T4); the white ramus communicans; the first, second, third, or fourth thoracic sympathetic ganglia; the thoracic sympathetic trunk; the cervical sympathetic trunk; a thoracic sympathetic cardiac nerve (stellate ganglia); and myocardial sympathetic nerves/beta adrenergic receptors.

In one embodiment, an implantable device is configured to deliver stimulation to one or more stimulation sites in timed relation to a cardiac depolarization such that the stimulation occurs during a selected part of the cardiac cycle. For example, sympathetic stimulation may be delivered during the absolute refractory period at a specified delay interval (e.g., 200 ms) after start of cardiac depolarization, either as a result of intrinsic activation or a pacing pulse. The device may be further configured to vary the specified delay interval with heart rate. For example, the specified delay interval may be shortened as the intrinsic or paced heart rate increases.

Besides the positive effect on lusitropy discussed above, sympathetic stimulation also has positive inotropic and chronotropic effects on the heart. It may be desired to supply sympathetic stimulation to the heart to increase lusitropy but without increasing the intrinsic heart rate, in which case the stimulation may be delivered to sympathetic nerves that innverate the ventricles but not the atria, particularly the sinoatrial node. Such stimulation may then be delivered on a chronic basis, either continuously (i.e., every cardiac cycle) or intermittently according to a defined schedule, in order to provide a conditioning effect. Stimulation could also be delivered to sympathetic nerves that innervate the atria, in addition to stimulation of ventricular sympathetic innvervation, in accordance with a measured exertion level so that the resulting positive chronotropic effect is appropriate. For example, an exemplary device could be equipped with an exertion level sensor (e.g., an accelerometer or minute ventilation sensor) and pulse generation circuitry connectable to an electrode disposed to stimulate atrial and ventricular sympathetic innervations. The device could then be configured to deliver the atrial and ventricular stimulation only if the measured exertion level is above a specified threshold level or configured to otherwise adjust stimulation parameters (e.g., duty cycle or pulse amplitude) so that the amount of stimulation increases with the measured exertion level. The device could also be configured to in addition deliver stimulation to electrodes disposed at sympathetic nerves that innverate only the ventricles on a chronic basis as described above.

Electrostimulation of sympathetic nervous tissue as described above could also be delivered as part of a closed-loop system that includes one or more sensing modalities for sensing a lusitropy parameter indicative of changes in myocardial relaxation. Examples of such measurable lusitropy parameters include a rate of pressure decline (−dP/dtmin) during diastole as determined from pressure sensor measurements, a rate of force/strain decline (−dF/dt) as determined from force sensor measurements, and isovolumic relaxation time (IVRT) as determined from cardiac impedance measurements or from detected heart sounds. The device may be programmed to compare the lusitropy parameter to a specified threshold in order to determine if diastolic relaxation is impaired and operate the neural stimulation circuitry to deliver sympathetic stimulation to the heart in response to thereto. Such measurements of a lusitropy parameter may also be used by the device to provide automated therapy optimization (e.g., adjustment of stimulation parameters and/or stimulation sites (electronic repositioning) in accordance with a determination of therapy efficacy based upon the lusitropy parameter(s).

The cardiosympathetic stimulation described above for the purpose of increasing cardiac lusitropy may be delivered by a device configured to also deliver other types of therapies. For example, the device may be equipped with a His-bundle pacing lead for direct pacing of the Purkinje network in order to excite myocardial beta adrenergic receptors. The device could then deliver His-bundle pacing in conjunction with sympathetic stimulation to augment relaxation. The device may also be configured to deliver other types of pacing for the purpose of improving cardiac function such as bradycardia pacing, resynchronization pacing, or high-output pacing (HOP) with high amplitude and/or long duration pacing pulses.

Exemplary Cardiac Device

An exemplary implantable cardiac device for delivering neural stimulation as described above would be placed subcutaneously or submuscularly in a patient's chest with leads threaded intravenously or otherwise placed to connect the device to electrodes or other types of sensors that are used for sensing and/or stimulating particular tissue. A programmable electronic controller controls the delivery of the electrostimulation. For example, if the device is configured to deliver cardiac pacing, the controller controls the delivery of pacing pulses in accordance to lapsed time intervals and/or sensed electrical activity (i.e., intrinsic heart beats not as a result of a pacing pulse). Once the device and leads are implanted, the stimulation and/or sensing channels of the device may be configured with selected ones of the multiple electrodes in order to selectively stimulate or sense particular tissue. The stimulation channels may be used to deliver conventional pacing or other stimulatory therapy to the heart or to deliver neural stimulation.

Figure 1:
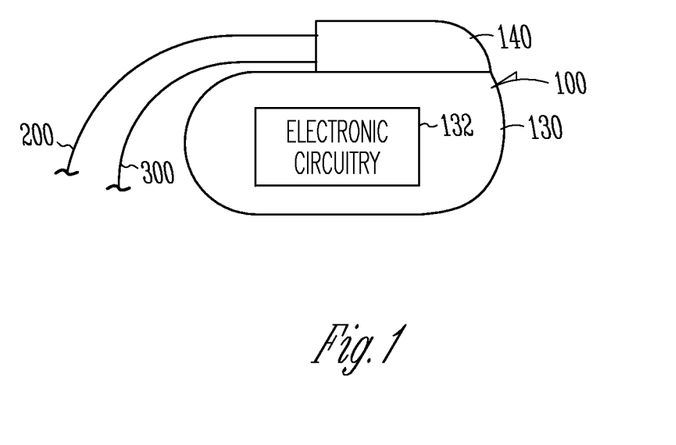
FIG. 1 shows the components of an exemplary device.

FIG. 1 shows the components of an implantable device 100 in more detail. The implantable device 100 includes a hermetically sealed housing 130 that may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device.

Figure 2:
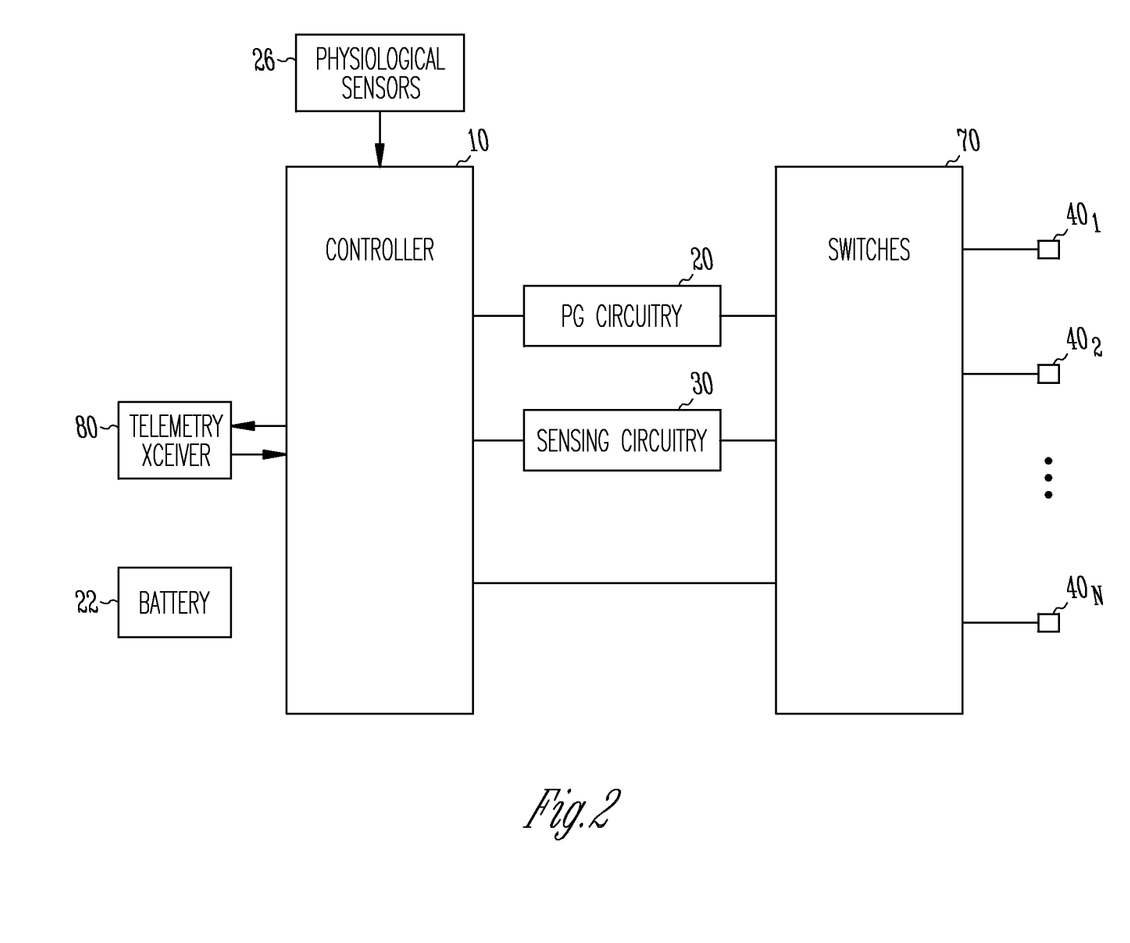
FIG. 2 is a block diagram of the electronic circuitry of an exemplary device.

FIG. 2 shows a system diagram of the electronic circuitry 132. A battery 22 supplies power to the circuitry. The controller 10 controls the overall operation of the device in accordance with programmed instructions and/or circuit configurations, including decisions as to the time and manner of stimulation pulses through the stimulation channels. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. Interfaced to the controller are sensing circuitry 30 and pulse generation circuitry 20 by which the controller interprets sensing signals and controls the delivery of paces and/or other stimulation pulses in accordance with a particular stimulation algorithm. A telemetry transceiver 80 is interfaced to the controller which enables the controller to communicate with an external device such as an external programmer and/or a remote monitoring unit.

The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively. The pulse generation circuitry 20 delivers pacing or other stimulation pulses to electrodes disposed in the heart or elsewhere and includes capacitive discharge or current source pulse generators, registers for controlling the pulse generators, and registers for adjusting parameters such as pulse energy (e.g., pulse amplitude and width).

A stimulation channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or stimulation channels. The switch matrix 70 also allows selected ones of the available implanted electrodes to be incorporated into sensing and/or stimulation channels in either unipolar or bipolar configurations.

The device may also include one or more physiological sensing modalities 26 for use in controlling the delivery of sympathetic stimulation as described above. One such sensing modality is an accelerometer that enables the controller to detect changes in the patient's physical activity for use as a measure of the patient's exertion level. Another measure of exertion level is minute ventilation. Exertion level measurements are conventionally used in rate-adaptive pacing modes used for chronotropically incompetent patients where the controller adapts the pacing rate in accordance with the measured exertion level. An impedance sensor may be configured with electrodes for measuring minute ventilation for use in measuring exertion and/or for measuring cardiac stroke volume or cardiac output. An accelerometer or a dedicated acoustic sensor that may be of various types may also be used to detect heart sounds. An accelerometer or other type of force sensor may be used for sensing myocardial tension or force. The device may also include a pressure sensor that may be used, for example, to measure pressure in the pulmonary artery or elsewhere.

Exemplary Embodiments

An exemplary device for delivering sympathetic stimulation to improve lusitropy as described above includes neural stimulation circuitry for delivering electrostimulation pulses to one or more electrodes adapted for stimulating sympathetic nerves innervating the heart and a controller for operating the neural stimulation circuitry. The device may also include cardiac sensing circuitry for connecting to one or more electrodes to sense cardiac electrical activity. The device is configured to operate in a neural stimulation mode in which the electrostimulation pulses are delivered in some specified manner. The device may also be equipped with additional components and be programmed to deliver sympathetic stimulation in various manners as described below with respect to different embodiments, the features of which may be combined in any manner found to be advantageous.

Figure 3:
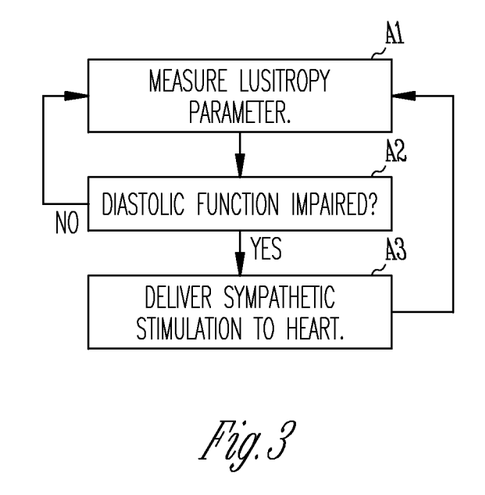
FIGS. 3 and 4 illustrate exemplary treatment algorithms.

In one embodiment, the device is configured to deliver sympathetic stimulation to the heart in dependence upon a measured lusitropy parameter indicative of diastolic dysfunction. An example of the treatment algorithm is illustrated in FIG. 3 where the device iteratively measures a lusitropy parameter at step A1, determines if diastolic function is impaired at step A2, and enters the neural stimulation mode for delivering sympathetic stimulation to the heart at step A3 if diastolic dysfunction is present. An exemplary device according to this embodiment includes lusitropy sensing circuitry for connecting to a lusitropy sensor and measuring a lusitropy parameter during diastole where the lusitropy parameter may be a rate of ventricular pressure decrease, a rate of ventricular force decrease, or ventricular isovolumic relaxation time. The lusitropy sensor may be a pressure sensor, an impedance sensor, a force sensor, or a heart sound sensor. For example, the lusitropy sensing circuitry may be configured to measure ventricular isovolumic relaxation time as indicated by an impedance sensor for measuring ventricular volume or as the interval between aortic valve closure and mitral valve opening as detected by a heart sound sensor. The controller is then programmed to compare the lusitropy parameter to a specified threshold in order to determine if diastolic relaxation is impaired and, if diastolic relaxation is impaired, enter the neural stimulation mode for operating the neural stimulation circuitry to deliver sympathetic stimulation to the heart. The controller may be further programmed to adjust one or more neural stimulation parameters selected from a neural stimulation duty cycle, an electrostimulation pulse amplitude, or particular electrodes to which the neural stimulation is delivered in accordance with the measured lusitropy parameter. For example, if the lusitropy parameter does not improve as a result of sympathetic stimulation being delivered for some period of time, the controller could adjust one or more of the neural stimulation parameters according to some predefined scheme.

Figure 4:
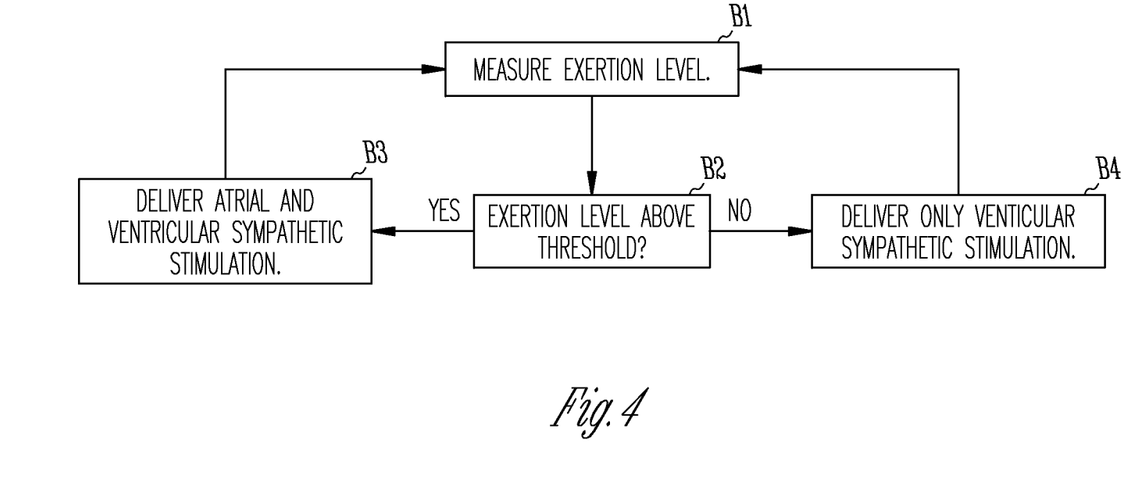

In another embodiment, the device is configured to, in the neural stimulation mode, deliver either stimulation to only ventricular sympathetic nerves or to atrial and ventricular sympathetic nerves in dependence upon a patient's measured exertion level. FIG. 4 illustrates an exemplary treatment algorithm where, in the neural stimulation mode, the device iteratively measures the patient's exertion level at step B1, compares the exertion level with a threshold at step B2, delivers atrial and ventricular sympathetic stimulation at step B3 if the exertion level is above the threshold, and delivers only ventricular sympathetic stimulation at step B4 if the exertion level is not above the threshold. An exemplary device in this embodiment includes an exertion level sensor selected from an accelerometer or a minute ventilation sensor, and neural stimulation circuitry configured to deliver electrostimulation pulses to an atrial stimulation channel configured to stimulate atrial sympathetic nerves and/or to a ventricular stimulation channel configured to stimulate ventricular sympathetic nerves. The controller is then configured to operate the neural stimulation circuitry in the neural stimulation mode so as to deliver electrostimulation pulses through both the atrial and ventricular stimulation channels if the exertion level is above a specified threshold value and deliver electrostimulation pulses through only the ventricular stimulation if the exertion level is not above the specified threshold value. The controller may also be configured to deliver electrostimulation pulses through the ventricular stimulation channel on an intermittent basis in the neural stimulation mode to exert a conditioning effect if the exertion level is not above the specified threshold value.

Other embodiments could include any of the following in the neural simulation mode. The device controller may be programmed to operate the neural stimulation circuitry to deliver electrostimulation pulses during a cardiac refractory period occurring at specified time interval after a detected cardiac depolarization. The device controller could be programmed to vary the specified time interval for delivering electrostimulation pulses with heart rate. The device could further include an accelerometer adapted for subcutaneous disposition in order to detect skeletal muscle contraction, and the controller is programmed to adjust one or more neural stimulation parameters if skeletal muscle contraction is detected. The controller may be programmed to measure heart rate during delivery of sympathetic stimulation and to discontinue the neural stimulation mode and delivery of sympathetic stimulation if the heart rate increases above a specified safety threshold value. The controller could be programmed to measure heart rate during delivery of sympathetic stimulation and to continue delivery of sympathetic stimulation if no heart rate increase and no change in the lusitropy parameter occurs in response thereto. The assumption here is that the lack of heart increase is good enough, and the changes in lusitrophy might not be measurable in each patient.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A device, comprising:
   neural stimulation circuitry for delivering electrostimulation pulses to one or more electrodes adapted for stimulating sympathetic nerves innervating the heart of a patient;
   lusitropy sensing circuitry for measuring a lusitropy parameter during diastole wherein the lusitropy parameter is selected from a rate of ventricular pressure decrease, a rate of ventricular force decrease, or isovolumic relaxation time;
   a controller programmed to compare the measured lusitropy parameter to a specified threshold in order to determine if diastolic relaxation is impaired and, when diastolic relaxation is impaired, enter a neural stimulation mode for operating the neural stimulation circuitry to deliver sympathetic stimulation to the heart; and,
   cardiac sensing circuitry for connecting to one or more electrodes to sense cardiac electrical activity and wherein the controller is connected to the cardiac sensing circuitry and programmed to measure heart rate during delivery of sympathetic stimulation and to discontinue the neural stimulation mode when the heart rate increases above a specified safety threshold value.

2. The device of claim 1 further comprising cardiac sensing circuitry for connecting to one or more electrodes to sense cardiac electrical activity and wherein the controller is connected to the cardiac sensing circuitry and programmed to deliver sympathetic stimulation to the heart by operating the neural stimulation circuitry to deliver electrostimulation pulses during a cardiac refractory period occurring at specified time interval after a detected cardiac depolarization.

3. The device of claim 2 wherein the controller is programmed to vary the specified time interval for delivering electrostimulation pulses with heart rate.

4. The device of claim 1 further comprising:
   an exertion level sensor selected from an accelerometer or a minute ventilation sensor for measuring the patient's exertion level;
   an atrial stimulation channel and a ventricular stimulation channel both connected to the neural stimulation circuitry, wherein the atrial stimulation channel is configured to stimulate atrial sympathetic nerves and the ventricular stimulation channel is configured to stimulate ventricular sympathetic nerves;
   wherein, in the neural stimulation mode, the controller is programmed to deliver electrostimulation pulses through both the atrial and ventricular stimulation channels when the exertion level is above a specified threshold value and deliver electrostimulation pulses through only the ventricular stimulation channel when the exertion level is not above the specified threshold value.

5. The device of claim 4 wherein, in the neural stimulation mode, the controller is configured to deliver electrostimulation pulses through the ventricular stimulation channel on an intermittent basis to exert a conditioning effect when the exertion level is not above the specified threshold value.

6. The device of claim 1 wherein the controller is further programmed to adjust a neural stimulation duty cycle in accordance with the measured rate of ventricular pressure decrease.

7. The device of claim 1 wherein the controller is further programmed to adjust an electrostimulation pulse amplitude in accordance with the measured rate of ventricular pressure decrease.

8. The device of claim 1 further comprising an accelerometer adapted for subcutaneous disposition in order to detect skeletal muscle contraction and wherein the controller is programmed to adjust one or more neural stimulation parameters when skeletal muscle contraction is detected.

9. The device of claim 1 wherein the controller is connected to the cardiac sensing circuitry and programmed to measure heart rate during delivery of sympathetic stimulation and to continue delivery of sympathetic stimulation when no heart rate increase and no change in the measured rate of ventricular pressure decrease occurs in response thereto.

10. A method for operating an implantable device in a patient, comprising:
    measuring a lusitropy parameter during diastole wherein the lusitropy parameter is selected from a rate of ventricular pressure decrease, a rate of ventricular force decrease, or an isovolumic relaxation time;
    comparing the measured lusitropy parameter to a specified threshold in order to determine if diastolic relaxation is impaired and, when diastolic relaxation is impaired, entering a neural stimulation mode to deliver electrostimulation pulses to one or more electrodes adapted for stimulating sympathetic nerves innervating the heart; and,
    measuring heart rate during delivery of sympathetic stimulation and discontinuing the neural stimulation mode when the heart rate increases above a specified safety threshold value.

11. The method of claim 10 further comprising delivering sympathetic stimulation to the heart by delivering electrostimulation pulses during a cardiac refractory period occurring at specified time interval after a detected cardiac depolarization.

12. The method of claim 11 further comprising varying the specified time interval for delivering electrostimulation pulses with heart rate.

13. The method of claim 10 further comprising:
    measuring the patient's exertion level;
    delivering electrostimulation pulses either through an atrial stimulation channel configured to stimulate atrial sympathetic nerves or through a ventricular stimulation channel configured to stimulate ventricular sympathetic nerves; and, in the neural stimulation mode, delivering electrostimulation pulses through both the atrial and ventricular stimulation channels when the exertion level is above a specified threshold value and delivering electrostimulation pulses through only the ventricular stimulation channel when the exertion level is not above the specified threshold value.

14. The method of claim 13 further comprising, in the neural stimulation mode, delivering electrostimulation pulses through the ventricular stimulation channel on an intermittent basis to exert a conditioning effect when the exertion level is not above the specified threshold value.

15. The method of claim 10 further comprising adjusting a neural stimulation duty cycle in accordance with the measured rate of ventricular pressure decrease.

16. The method of claim 10 further comprising adjusting an electrostimulation pulse amplitude in accordance with the measured rate of ventricular pressure decrease.

17. The method of claim 10 further comprising detecting skeletal muscle contraction and adjusting one or more neural stimulation parameters when skeletal muscle contraction is detected.

18. The method of claim 10 further comprising measuring heart rate during delivery of sympathetic stimulation and continuing delivery of sympathetic stimulation when no heart rate increase and no change in the measured rate of ventricular pressure decrease occurs in response thereto.

* * * * *